(12) United States Patent
Hawkins

(10) Patent No.: US 11,517,338 B2
(45) Date of Patent: *Dec. 6, 2022

(54) DRUG DELIVERY SHOCK WAVE BALLOON CATHETER SYSTEM

(71) Applicant: Shockwave Medical, Inc., Santa Clara, CA (US)

(72) Inventor: Daniel Hawkins, Santa Clara, CA (US)

(73) Assignee: SHOCKWAVE MEDICAL, INC., Santa Clara, CA (US)

(*) Notice: Subject to any disclaimer, the term of this patent is extended or adjusted under 35 U.S.C. 154(b) by 417 days.

This patent is subject to a terminal disclaimer.

(21) Appl. No.: 16/569,303

(22) Filed: Sep. 12, 2019

(65) Prior Publication Data

US 2020/0000484 A1 Jan. 2, 2020

Related U.S. Application Data

(63) Continuation of application No. 15/491,408, filed on Apr. 19, 2017, now Pat. No. 10,441,300.

(51) Int. Cl.
*A61B 17/22* (2006.01)
*A61M 25/10* (2013.01)
(Continued)

(52) U.S. Cl.
CPC ...... *A61B 17/2202* (2013.01); *A61K 41/0028* (2013.01); *A61K 47/6957* (2017.08);
(Continued)

(58) Field of Classification Search
CPC ...... A61B 17/2202; A61B 2017/00703; A61B 2017/003; A61B 2017/22021;
(Continued)

(56) References Cited

U.S. PATENT DOCUMENTS 3,785,382 A 1/1974 Schmidt-Kloiber et al.
3,902,499 A 9/1975 Shene
(Continued)

FOREIGN PATENT DOCUMENTS

DE 3038445 A1 5/1982
EP 0442199 A2 8/1991
(Continued)

OTHER PUBLICATIONS

Stephen Levin, Shockwave Medical: Cracking the Calcium Code in Cardiology. 2:14 MedTech Strategist 30-37, published Aug. 12, 2015.*
(Continued)

*Primary Examiner* — Theodore J Stigell
(74) *Attorney, Agent, or Firm* — Morrison & Foerster LLP

(57) ABSTRACT

A catheter comprises an elongated carrier and a balloon carried by the carrier in sealed relation thereto. The balloon has an outer surface and is arranged to receive a fluid therein that inflates the balloon. The catheter further comprises a shock wave generator within the balloon that forms mechanical shock waves within the balloon, and a medicinal agent carried on the outer surface of the balloon. The medicinal agent is releasable from the balloon either before or in response to the shock wave.

7 Claims, 8 Drawing Sheets

(51) Int. Cl.
   *A61L 29/16* (2006.01)
   *A61K 41/00* (2020.01)
   *A61K 47/69* (2017.01)
   *A61M 37/00* (2006.01)
   *A61B 17/00* (2006.01)

(52) U.S. Cl.
   CPC ........... *A61L 29/16* (2013.01); *A61M 25/104* (2013.01); *A61B 2017/003* (2013.01); *A61B 2017/00703* (2013.01); *A61B 2017/22021* (2013.01); *A61B 2017/22024* (2013.01); *A61B 2017/22025* (2013.01); *A61B 2017/22061* (2013.01); *A61B 2017/22062* (2013.01); *A61B 2017/22084* (2013.01); *A61B 2017/22088* (2013.01); *A61L 2300/622* (2013.01); *A61M 37/0092* (2013.01); *A61M 2025/105* (2013.01)

(58) Field of Classification Search
   CPC ........... A61B 2017/22024; A61B 2017/22061; A61B 2017/22062; A61B 2017/22084; A61B 2017/22088; A61M 37/0092; A61M 2025/105; A61M 25/104
   See application file for complete search history.

(56) References Cited

U.S. PATENT DOCUMENTS

| | | | |
|---|---|---|---|
| 4,027,674 A | 6/1977 | Tessier et al. | |
| 4,662,126 A | 5/1987 | Malcolm | |
| 4,685,458 A | 8/1987 | Leckrone | |
| 4,809,682 A | 3/1989 | Forssmann et al. | |
| 4,900,303 A | 2/1990 | Lemelson | |
| 5,009,232 A | 4/1991 | Hassler et al. | |
| 5,057,103 A | 10/1991 | Davis | |
| 5,078,717 A | 1/1992 | Parins et al. | |
| 5,102,402 A | 4/1992 | Dror et al. | |
| 5,103,804 A | 4/1992 | Abele et al. | |
| 5,152,767 A | 10/1992 | Sypal et al. | |
| 5,152,768 A | 10/1992 | Bhatta | |
| 5,176,675 A | 1/1993 | Watson et al. | |
| 5,246,447 A | 9/1993 | Rosen et al. | |
| 5,281,231 A | 1/1994 | Rosen et al. | |
| 5,324,255 A | 6/1994 | Passafaro et al. | |
| 5,336,234 A | 8/1994 | Vigil et al. | |
| 5,368,591 A | 11/1994 | Lennox et al. | |
| 5,395,335 A | 3/1995 | Jang | |
| 5,417,208 A | 5/1995 | Winkler | |
| 5,425,735 A | 6/1995 | Rosen et al. | |
| 5,472,406 A | 12/1995 | De La Torre et al. | |
| 5,582,578 A | 12/1996 | Zhong et al. | |
| 5,603,731 A | 2/1997 | Whitney | |
| 5,609,606 A | 3/1997 | O'Boyle | |
| 5,662,590 A | 9/1997 | De La Torre et al. | |
| 5,674,192 A | 10/1997 | Sahatjian et al. | |
| 5,893,840 A | 4/1999 | Hull et al. | |
| 5,931,805 A | 8/1999 | Brisken | |
| 6,007,530 A | 12/1999 | Dörnhöfer et al. | |
| 6,033,371 A | 3/2000 | Torre et al. | |
| 6,083,232 A | 7/2000 | Cox | |
| 6,146,358 A | 11/2000 | Rowe | |
| 6,210,408 B1 | 4/2001 | Chandrasekaran et al. | |
| 6,217,531 B1 | 4/2001 | Reitmajer | |
| 6,277,138 B1 | 8/2001 | Levinson et al. | |
| 6,287,272 B1 | 9/2001 | Brisken et al. | |
| 6,352,535 B1 | 3/2002 | Lewis et al. | |
| 6,352,683 B1 † | 3/2002 | Ten Cate | |
| 6,367,203 B1 | 4/2002 | Graham et al. | |
| 6,371,971 B1 | 4/2002 | Tsugita et al. | |
| 6,398,792 B1 | 6/2002 | O'Connor | |
| 6,406,486 B1 | 6/2002 | De La Torre et al. | |
| 6,514,203 B2 | 2/2003 | Bukshpan | |
| 6,524,251 B2 | 2/2003 | Rabiner et al. | |
| 6,589,253 B1 | 7/2003 | Cornish et al. | |
| 6,607,003 B1 | 8/2003 | Wilson | |
| 6,638,246 B1 | 10/2003 | Naimark et al. | |
| 6,652,547 B2 † | 11/2003 | Rabiner | |
| 6,736,784 B1 | 5/2004 | Menne et al. | |
| 6,740,081 B2 | 5/2004 | Hilal | |
| 6,755,821 B1 | 6/2004 | Fry | |
| 6,939,320 B2 | 9/2005 | Lennox | |
| 6,989,009 B2 | 1/2006 | Lafontaine | |
| 7,066,904 B2 | 6/2006 | Rosenthal et al. | |
| 7,241,295 B2 | 7/2007 | Maguire | |
| 7,569,032 B2 | 8/2009 | Naimark et al. | |
| 8,556,813 B2 | 10/2013 | Cioanta et al. | |
| 8,728,091 B2 | 5/2014 | Hakala et al. | |
| 8,888,788 B2 | 11/2014 | Hakala et al. | |
| 9,138,249 B2 | 9/2015 | Adams et al. | |
| 9,180,280 B2 | 11/2015 | Hawkins et al. | |
| 9,333,000 B2 | 5/2016 | Hakala et al. | |
| 9,433,428 B2 | 9/2016 | Hakala et al. | |
| 9,522,012 B2 | 12/2016 | Adams | |
| 9,642,673 B2 | 5/2017 | Adams et al. | |
| 10,327,846 B1 † | 6/2019 | Stark | |
| 10,441,300 B2 * | 10/2019 | Hawkins | A61K 47/6957 |
| 2001/0044596 A1 | 11/2001 | Jaafar | |
| 2002/0177889 A1 | 11/2002 | Brisken et al. | |
| 2003/0004434 A1 | 1/2003 | Greco et al. | |
| 2003/0176873 A1 | 9/2003 | Chernenko et al. | |
| 2003/0229370 A1 | 12/2003 | Miller | |
| 2004/0044308 A1 | 3/2004 | Naimark et al. | |
| 2004/0097996 A1 | 5/2004 | Rabiner et al. | |
| 2004/0254570 A1 | 12/2004 | Hadjicostis et al. | |
| 2005/0015953 A1 | 1/2005 | Keidar | |
| 2005/0021013 A1 | 1/2005 | Visuri et al. | |
| 2005/0251131 A1 | 11/2005 | Lesh | |
| 2006/0004286 A1 | 1/2006 | Chang et al. | |
| 2006/0184076 A1 | 8/2006 | Gill et al. | |
| 2006/0190022 A1 | 8/2006 | Beyar et al. | |
| 2007/0088380 A1 | 4/2007 | Hirszowicz et al. | |
| 2007/0239082 A1 | 10/2007 | Schultheiss et al. | |
| 2007/0239253 A1 | 10/2007 | Jagger et al. | |
| 2007/0244423 A1 | 10/2007 | Zumeris et al. | |
| 2008/0097251 A1 | 4/2008 | Babaev | |
| 2008/0188913 A1 | 8/2008 | Stone et al. | |
| 2009/0041833 A1 | 2/2009 | Bettinger et al. | |
| 2009/0247945 A1 | 10/2009 | Levit et al. | |
| 2009/0254114 A1 | 10/2009 | Hirszowicz et al. | |
| 2009/0312768 A1 | 12/2009 | Hawkins et al. | |
| 2010/0016862 A1 | 1/2010 | Hawkins et al. | |
| 2010/0036294 A1 | 2/2010 | Mantell et al. | |
| 2010/0114020 A1 | 5/2010 | Hawkins et al. | |
| 2010/0114065 A1 * | 5/2010 | Hawkins | A61M 25/1006 604/509 |
| 2010/0121322 A1 | 5/2010 | Swanson | |
| 2010/0305565 A1 | 12/2010 | Truckai et al. | |
| 2011/0034832 A1 | 2/2011 | Cioanta et al. | |
| 2011/0118634 A1 | 5/2011 | Golan | |
| 2011/0166570 A1 | 7/2011 | Hawkins et al. | |
| 2011/0257523 A1 | 10/2011 | Hastings et al. | |
| 2011/0295227 A1 | 12/2011 | Hawkins et al. | |
| 2012/0071889 A1 | 3/2012 | Mantell et al. | |
| 2012/0095461 A1 | 4/2012 | Herscher et al. | |
| 2012/0203255 A1 | 8/2012 | Hawkins et al. | |
| 2012/0221013 A1 | 8/2012 | Hawkins et al. | |
| 2013/0030431 A1 | 1/2013 | Adams | |
| 2013/0030447 A1 | 1/2013 | Adams | |
| 2013/0150874 A1 | 6/2013 | Kassab | |
| 2014/0031800 A1 † | 1/2014 | Ben Oren | |
| 2014/0046229 A1 | 2/2014 | Hawkins et al. | |
| 2014/0052147 A1 | 2/2014 | Hakala et al. | |
| 2014/0074111 A1 | 3/2014 | Hakala et al. | |
| 2014/0243820 A1 | 8/2014 | Adams et al. | |
| 2014/0243847 A1 | 8/2014 | Hakala et al. | |
| 2016/0184570 A1 | 6/2016 | Grace et al. | |
| 2017/0265942 A1 * | 9/2017 | Grace | A61B 18/245 |
| 2019/0262594 A1 † | 8/2019 | Ogata | |

FOREIGN PATENT DOCUMENTS

| | | | |
|---|---|---|---|
| EP | 0571306 | † | 11/1993 |
| EP | 0571306 A1 | | 11/1993 |
| JP | 62-275446 A | | 11/1987 |

(56) References Cited

FOREIGN PATENT DOCUMENTS

| JP | 6-125915 A | 5/1994 |
|---|---|---|
| JP | 7-47135 A | 2/1995 |
| JP | 10-99444 A | 4/1998 |
| JP | 10-513379 A | 12/1998 |
| JP | 2002-538932 A | 11/2002 |
| JP | 2004-81374 A | 3/2004 |
| JP | 2005-95410 A | 4/2005 |
| JP | 2005-515825 A | 6/2005 |
| JP | 2006-516465 A | 7/2006 |
| WO | 92/11890 † | 7/1992 |
| WO | 1996/24297 A1 | 8/1996 |
| WO | 2002/043796 A2 | 6/2002 |
| WO | 2004/069072 A2 | 8/2004 |
| WO | 2006/127158 A2 | 11/2006 |
| WO | 2007/149905 A2 | 12/2007 |
| WO | 2009/121017 A1 | 10/2009 |
| WO | 2009/152352 A2 | 12/2009 |
| WO | 2010/014515 A2 | 2/2010 |
| WO | 2011/006017 A1 | 1/2011 |
| WO | 2011/143468 A2 | 11/2011 |
| WO | 2013/059735 A1 | 4/2013 |

OTHER PUBLICATIONS

International Preliminary Report on Patentability received for PCT Patent Application No. PCT/US2018/019176, dated Oct. 31, 2019, 6 pages.
Advisory Action received for U.S. Appl. No. 12/581,295, dated Jul. 3, 2014, 3 pages.
Advisory Action received for U.S. Appl. No. 13/267,383, dated Jan. 6, 2014, 4 pages.
Cleveland et al., "The Physics of Shock Wave Lithotripsy", Extracorporeal Shock Wave Lithotripsy Part IV, Chapter 38, 2012, pp. 317-332.
Connors et al., "Renal Nerves Mediate Changes in Contralateral Renal Blood Flow after Extracorporeal Shockwave Lithotripsy", Nephron Physiol, vol. 95, 2003, pp. 67-75.
Extended European Search Report (includes Supplementary European Search Report and Search Opinion) received for European Patent Application No. 09763640.1, dated Oct. 10, 2013, 5 pages.
Final Office Action received for U.S. Appl. No. 12/581,295, dated Mar. 28, 2013, 8 pages.
Final Office Action received for U.S. Appl. No. 12/482,995, dated Feb. 20, 2014, 11 pages.
Final Office Action received for U.S. Appl. No. 12/581,295, dated Jun. 5, 2014, 14 pages.
Final Office Action received for U.S. Appl. No. 13/049,199 dated Aug. 11, 2014, 8 pages.
Final Office Action received for U.S. Appl. No. 13/267,383, dated Oct. 25, 2013, 8 pages.
Final Office Action received for U.S. Appl. No. 15/491,408, dated Sep. 25, 2018, 8 pages.
Gambihler et al., "Permeabilization of the Plasma Membrane of L1210 Mouse Leukemia Cells Using Lithotripter Shock Waves", The Journal of Membrane Biology, vol. 141, 1994, pp. 267-275.
Grassi et al., "Novel Antihypertensive Therapies: Renal Sympathetic Nerve Ablation and Carotid Baroreceptor Stimulation", Curr Hypertens Rep vol. 14, 2012, pp. 567-572.
International Preliminary Report on Patentability received for PCT Patent Application No. PCT/US2009/047070, dated Dec. 23, 2010, 7 pages.
International Preliminary Report on Patentability received for PCT Patent Application No. PCT/US2011/047070, dated Feb. 21, 2013, 7 pages.
International Preliminary Report on Patentability received for PCT Patent Application No. PCT/US2012/023172, dated Aug. 15, 2013, 6 pages.
International Search Report and Written Opinion received for PCT Patent Application No. PCT/US2013/031805, dated May 20, 2013, 13 pages.
International Search Report and Written Opinion received for PCT Patent Application No. PCT/US2013/039987, dated Sep. 23, 2013, 15 pages.
International Search Report and Written Opinion received for PCT Patent Application No. PCT/US2013/048277, dated Oct. 2, 2013, 14 pages.
International Search Report and Written Opinion received for PCT Patent Application No. PCT/US2013/055431, dated Nov. 12, 2013, 9 pages.
International Search Report and Written Opinion received for PCT Patent Application No. PCT/US2013/059533, dated Nov. 7, 2013, 14 pages.
International Search Report received for PCT Patent Application No. PCT/US2009/047070, dated Jan. 19, 2010, 4 pages.
International Search Report received for PCT Patent Application No. PCT/US2012/023172, dated Sep. 28, 2012, 3 pages.
International Search Report and Written Opinion received for PCT Patent Application No. PCT/US2018/019176, dated May 2, 2018, 10 pages.
International Written Opinion received for PCT Patent Application No. PCT/US2009/047070, dated Jan. 19, 2010, 5 pages.
International Written Opinion received for PCT Patent Application No. PCT/US2011/047070, dated May 1, 2012, 5 pages.
Kodama et al., "Shock Wave-Mediated Molecular Delivery into Cells", Biochimica et Biophysica Acta vol. 1542, 2002, pp. 186-194.
Lauer et al., "Shock Wave Permeabilization as a New Gene Transfer Method", Gene Therapy, vol. 4, 1997, pp. 710-715.
Non-Final Office Action received for U.S. Appl. No. 12/482,995, dated Aug. 13, 2014, 10 pages.
Non-Final Office Action received for U.S. Appl. No. 12/482,995, dated Jul. 12, 2013, 11 pages.
Non-Final Office Action received for U.S. Appl. No. 13/465,264, dated Oct. 29, 2014, 13 pages.
Non-Final Office Action received for U.S. Appl. No. 13/646,570, dated Oct. 29, 2014, 10 pages.
Non-Final Office Action received for U.S. Appl. No. 14/079,463, dated Mar. 4, 2014, 9 pages.
Non-Final Office Action received for U.S. Appl. No. 12/581,295, dated Dec. 21, 2012, 9 pages.
Non-Final Office Action received for U.S. Appl. No. 12/581,295, dated Jun. 8, 2012, 9 pages.
Non-Final Office Action received for U.S. Appl. No. 12/501,619, dated Jan. 28, 2014, 10 pages.
Non-Final Office Action received for U.S. Appl. No. 12/581,295, dated Jan. 15, 2015, 14 pages.
Non-Final Office Action received for U.S. Appl. No. 12/581,295, dated Mar. 10, 2014, 11 pages.
Non-Final Office Action received for U.S. Appl. No. 13/049,199, dated Feb. 4, 2014, 8 pages.
Non-Final Office Action received for U.S. Appl. No. 13/646,583, dated Oct. 31, 2014, 8 pages.
Non-Final Office Action received for U.S. Appl. No. 14/061,554, dated Mar. 12, 2014, 14 pages.
Non-Final Office Action received for U.S. Appl. No. 14/271,276, dated Aug. 4, 2014, 7 pages.
Non-Final Office Action received for U.S. Appl. No. 14/271,342, dated Sep. 2, 2014, 6 pages.
Non-Final Office Action received for U.S. Appl. No. 15/491,408, dated Jan. 31, 2019, 9 pages.
Non-Final Office Action received for U.S. Appl. No. 15/491,408, dated May 15, 2018, 8 pages.
Notice of Allowance received for U.S. Appl. No. 15/491,408, dated Jun. 11, 2019, 7 pages.
Notice of Acceptance Received for Australian Patent Application No. 2009257368, dated Aug. 28, 2014, 2 pages.
Notice of Allowance received for U.S. Appl. No. 12/581,295, dated Jul. 10, 2015, 15 pages.
Notice of Allowance received for U.S. Appl. No. 12/581,295, dated Jul. 29, 2015, 7 pages.
Notice of Allowance received for U.S. Appl. No. 13/831,543, dated Oct. 8, 2014, 14 pages.

(56) References Cited

OTHER PUBLICATIONS

Notice of Allowance received for U.S. Appl. No. 14/061,554, dated Apr. 25, 2014, 8 pages.
Notice of Allowance received for U.S. Appl. No. 14/079,463, dated Apr. 1, 2014, 5 pages.
Office Action received for Australian Patent Application No. 2009257368, dated Apr. 28, 2014, 4 pages.
Office Action received for Australian Patent Application No. 2009257368, dated Jul. 31, 2013, 4 pages.
Office Action received for Japanese Patent Application No. 2011-513694, dated Aug. 27, 2013, 6 pages.
Office Action received for Japanese Patent Application No. 2011-513694, dated Jun. 10, 2014, 4 pages.
Rosenschein et al., "Shock-Wave Thrombus Ablation, A New Method for Noninvasive Mechanical Thrombolysis", The American Journal of Cardiology, vol. 70, Nov. 15, 1992, pp. 1358-1361.
Zhong et al., "Transient Oscillation of Cavitation Bubbles Near Stone Surface During Electrohydraulic Lithotripsy", Journal of Endourology, vol. 11, No. 1, Feb. 1997, pp. 55-61.

\* cited by examiner
† cited by third party

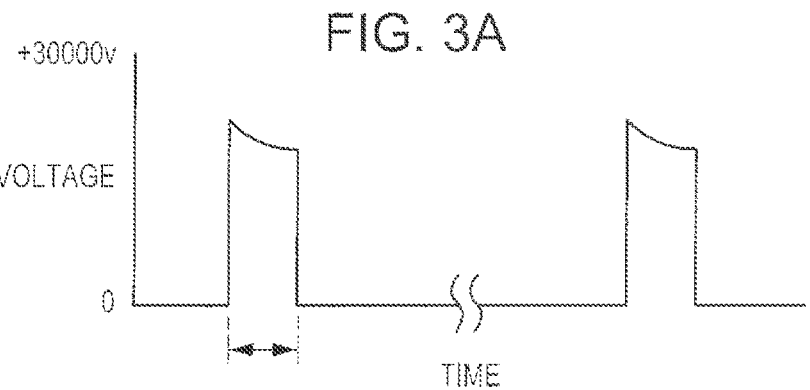
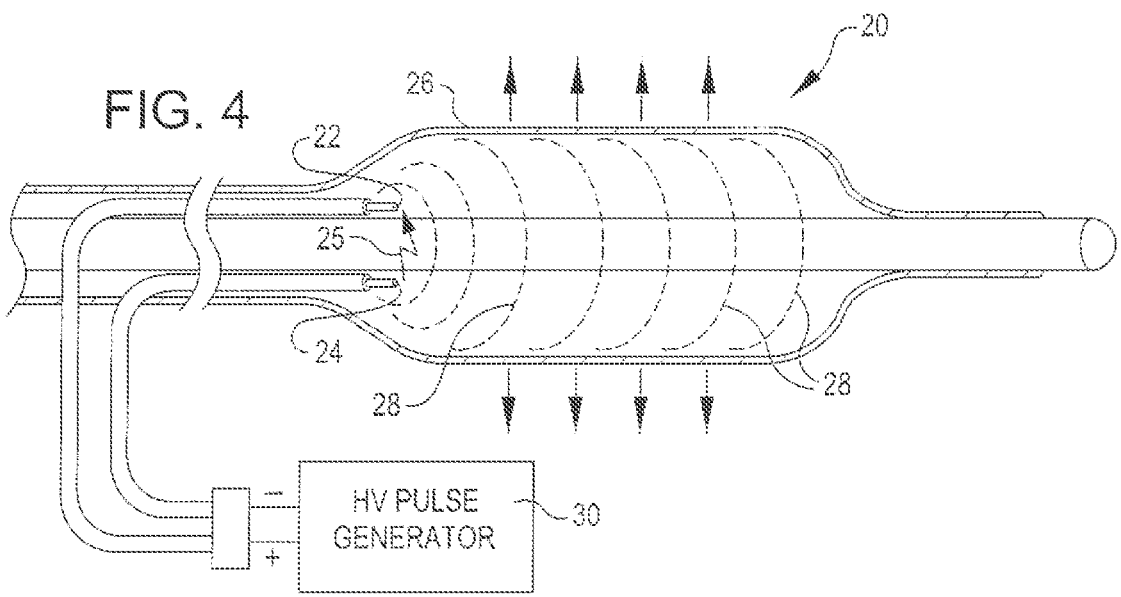
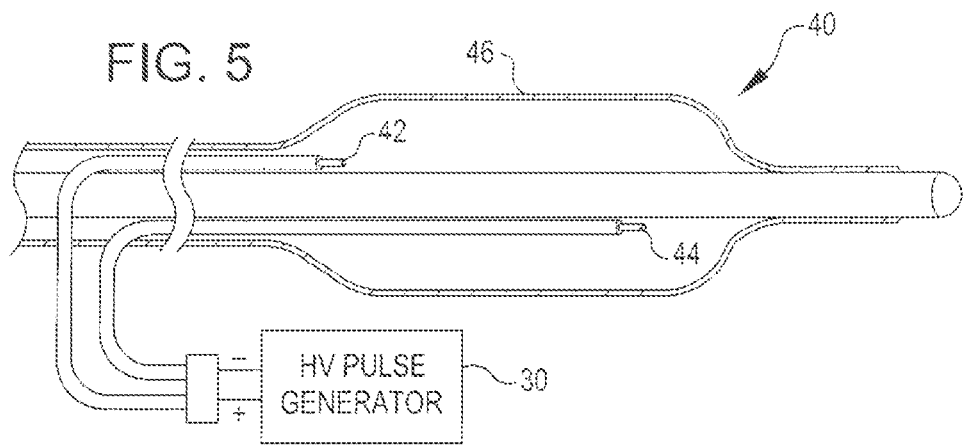

DRUG DELIVERY SHOCK WAVE BALLOON CATHETER SYSTEM

CROSS-REFERENCE TO RELATED APPLICATIONS

This application is a continuation of U.S. patent application Ser. No. 15/491,408, filed Apr. 19, 2017, which is hereby incorporated by reference in its entirety for all purposes.

BACKGROUND OF THE INVENTION

The present invention relates to a treatment system for percutaneous coronary angioplasty or peripheral angioplasty in which a dilation catheter is used to cross a lesion in order to dilate the lesion and restore normal blood flow in the artery. It is particularly useful when the lesion is a calcified lesion in the wall of the artery. Calcified lesions require high pressures (sometimes as high as 10-15 atmospheres) to break the calcified plaque and push it back into the vessel wall. With such pressures comes trauma to the vessel wall which can contribute to vessel rebound, dissection, thrombus formation, and a high level of restenosis. Non-concentric calcified lesions can result in undue stress to the free wall of the vessel when exposed to high pressures. An angioplasty balloon when inflated to high pressures can have a specific maximum diameter to which it will expand but the opening in the vessel under a concentric lesion will typically be much smaller. As the pressure is increased to open the passage way for blood the balloon will be confined to the size of the open in the calcified lesion (before it is broken open). As the pressure builds a tremendous amount of energy is stored in the balloon until the calcified lesion breaks or cracks. That energy is then released and results in the rapid expansion of the balloon to its maximum dimension and may stress and injure the vessel walls. Antiproliferative drugs such as Paclitaxel delivered to the site of balloon expansion or stent deployment is known to reduce the response of the vessel to the injury or the stent. Such drugs are currently coated on the stent surface and provide long term deployment to prevent restenosis due to cell proliferation.

SUMMARY OF THE INVENTION

In one embodiment, a catheter comprises an elongated carrier, a balloon carried by the carrier in sealed relation thereto, the balloon having an outer surface and being arranged to receive a fluid therein that inflates the balloon, and a shock wave generator within the balloon that forms mechanical shock waves within the balloon. The catheter further includes a medicinal agent carried on the outer surface of the balloon. The medicinal agent is releasable from the balloon by the shock waves.

The medicinal agent may be in the form of a plurality of microspheres. The microspheres may have a diameter of between about 2 microns and about 100 microns.

Alternatively, the medicinal agent may in the form of a plurality of microcapsules having a drug therein, wherein the drug is releasable from the microcapsules by the shock waves. The microcapsules may have a diameter of between about 2 microns and about 100 microns. The microcapsules may be arranged to crack open upon exposure to the shock waves. The microcapsules may be formed of a polymer, a starch, or glucose.

The medicinal agent may still alternatively be in the form of a layer of a drug bonded to the balloon outer surface.

According to another embodiment, a method comprises the step of providing a catheter having an elongated carrier and a balloon carried by the carrier in sealed relation thereto. The balloon has an outer surface. The method further comprises the steps of applying a medicinal agent to the outer surface of the balloon, inflating the balloon with a liquid, and producing mechanical shock waves within the balloon to release the medicinal agent from the balloon outer surface.

The applying step may include providing the medicinal agent in the form of a plurality of microspheres. The microspheres may be formed to have a diameter of between about 2 microns and about 100 microns.

The applying step may alternatively include providing the medicinal agent in the form of a plurality of microcapsules having a drug therein, wherein the drug is releasable from the microcapsules by the shock waves. The microcapsules may be formed to have a diameter of between about 2 microns and about 100 microns. The mechanical shocks waves are preferably provided with sufficient energy to cause the microcapsules to crack open to release the drug. The microcapsules are formed of a polymer, a starch, or glucose.

The applying step may further alternatively include providing the medicinal agent in the form of a layer of a drug bonded to the balloon outer surface.

BRIEF DESCRIPTION OF THE DRAWINGS

The features of the present invention which are believed to be novel are set forth with particularity in the appended claims. The various embodiments of the invention, together with representative features and advantages thereof, may best be understood by making reference to the following description taken in conjunction with the accompanying drawings, in the several figures of which like reference numerals identify identical elements, and wherein:

FIG. 3A shows voltage pulses that may be obtained with the generator of FIG. 3;

FIG. 4 is a side view of the catheter of FIG. 2 showing an arc between the electrodes and simulations of the shock wave flow;

FIG. 5 is a side view of a dilating catheter with insulated electrodes within the balloon and displaced along the length of the balloon according to another embodiment of the invention;

DETAILED DESCRIPTION OF THE INVENTION

Figure 1:
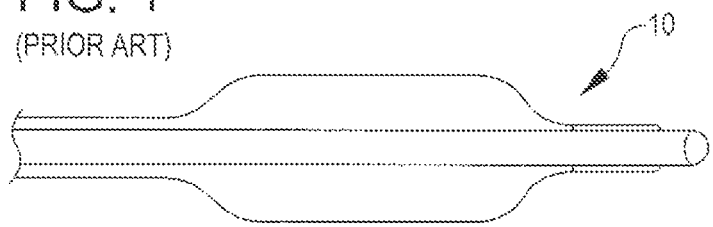
FIG. 1 is a view of the therapeutic end of a typical prior art over-the-wire angioplasty balloon catheter.

FIG. 1 is a view of the therapeutic end of a typical prior art over-the-wire angioplasty balloon catheter 10. Such catheters are usually non-complaint with a fixed maximum dimension when expanded with a fluid such as saline.

Figure 2:
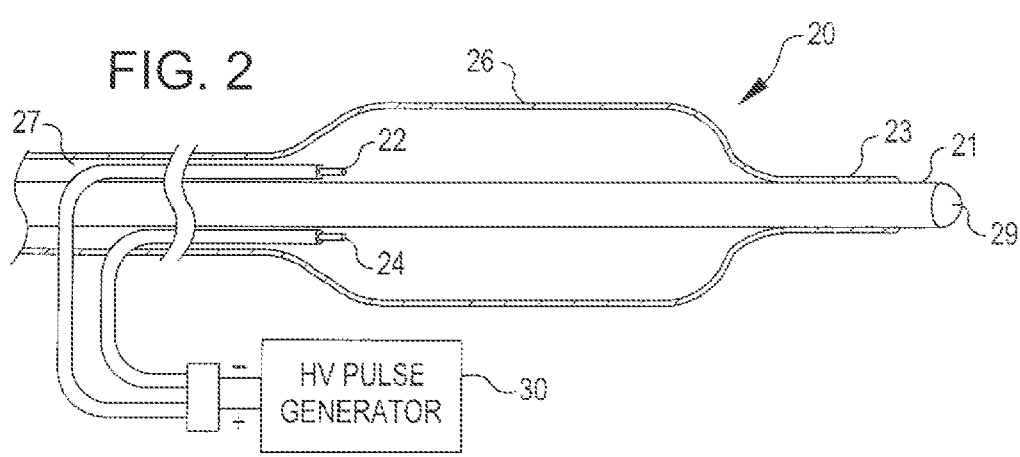
FIG. 2 is a side view of a dilating angioplasty balloon catheter with two electrodes within the balloon attached to a source of high voltage pulses according to one embodiment of the invention.

FIG. 2 is a view of a dilating angioplasty balloon catheter 20 according to an embodiment of the invention. The catheter 20 includes an elongated carrier, such as a hollow sheath 21, and a dilating balloon 26 formed about the sheath 21 in sealed relation thereto at a seal 23. The balloon 26 forms an annular channel 27 about the sheath 21 through which fluid, such as saline, may be admitted into the balloon to inflate the balloon. The channel 27 further permits the balloon 26 to be provided with two electrodes 22 and 24 within the fluid filled balloon 26. The electrodes 22 and 24 are attached to a source of high voltage pulses 30. The electrodes 22 and 24 are formed of metal, such as stainless steel, and are placed a controlled distance apart to allow a reproducible arc for a given voltage and current. The electrical arcs between electrodes 22 and 24 in the fluid are used to generate shock waves in the fluid. The variable high voltage pulse generator 30 is used to deliver a stream of pulses to the electrodes 22 and 24 to create a stream of shock waves within the balloon 26 and within the artery being treated (not shown). The magnitude of the shock waves can be controlled by controlling the magnitude of the pulsed voltage, the current, the duration and repetition rate. The insulating nature of the balloon 26 protects the patient from electrical shocks.

The balloon 26 may be filled with water or saline in order to gently fix the balloon in the walls of the artery in the direct proximity with the calcified lesion. The fluid may also contain an x-ray contrast to permit fluoroscopic viewing of the catheter during use. The carrier 21 includes a lumen 29 through which a guidewire (not shown) may be inserted to guide the catheter into position. Once positioned the physician or operator can start with low energy shock waves and increase the energy as needed to crack the calcified plaque. Such shock waves will be conducted through the fluid, through the balloon, through the blood and vessel wall to the calcified lesion where the energy will break the hardened plaque without the application of excessive pressure by the balloon on the walls of the artery.

Figure 3:
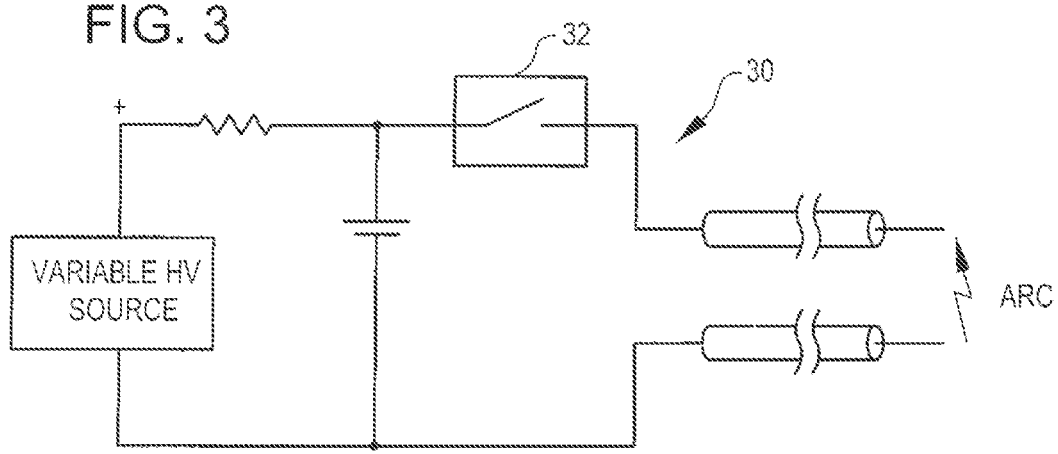
FIG. 3 is a schematic of a high voltage pulse generator.

FIG. 3 is a schematic of the high voltage pulse generator 30. FIG. 3A shows a resulting waveform. The voltage needed will depend on the gap between the electrodes and generally 100 to 3000 volts. The high voltage switch 32 can be set to control the duration of the pulse. The pulse duration will depend on the surface area of the electrodes 22 and 24 and needs to be sufficient to generate a gas bubble at the surface of the electrode causing a plasma arc of electric current to jump the bubble and create a rapidly expanding and collapsing bubble, which creates the mechanical shock wave in the balloon. Such shock waves can be as short as a few microseconds.

FIG. 4 is a cross sectional view of the shock wave catheter 20 showing an arc 25 between the electrodes 22 and 24 and simulations of the shock wave flow 28. The shock wave 28 will radiate out from the electrodes 22 and 24 in all directions and will travel through the balloon 26 to the vessel where it will break the calcified lesion into smaller pieces.

FIG. 5 shows another dilating catheter 40. It has insulated electrodes 42 and 44 within the balloon 46 displaced along the length of the balloon 46.

Figure 6:
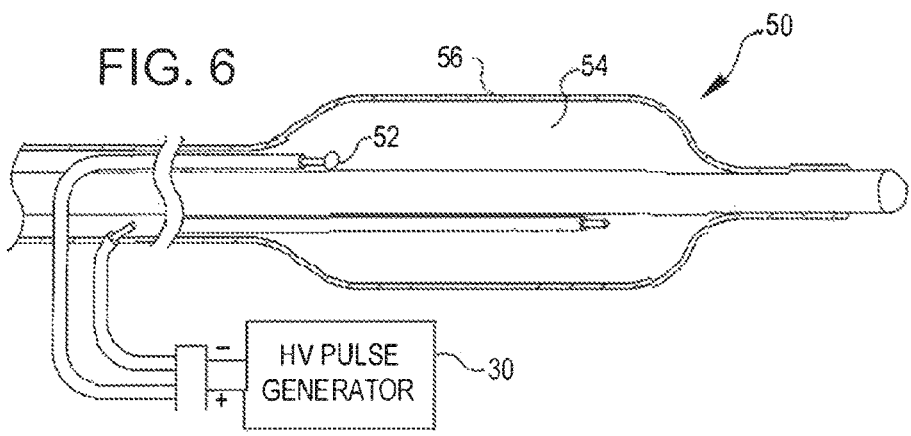
FIG. 6 is a side view of a dilating catheter with insulated electrodes within the balloon displaced with a single pole in the balloon and a second being the ionic fluid inside the balloon according to a further embodiment of the invention.

FIG. 6 shows a dilating catheter 50 with an insulated electrode 52 within the balloon 56. The electrode is a single electrode pole in the balloon, a second pole being the ionic fluid 54 inside the balloon. This unipolar configuration uses the ionic fluid as the other electrical pole and permits a smaller balloon and catheter design for low profile balloons. The ionic fluid is connected electrically to the HV pulse generator 30.

Figure 7:
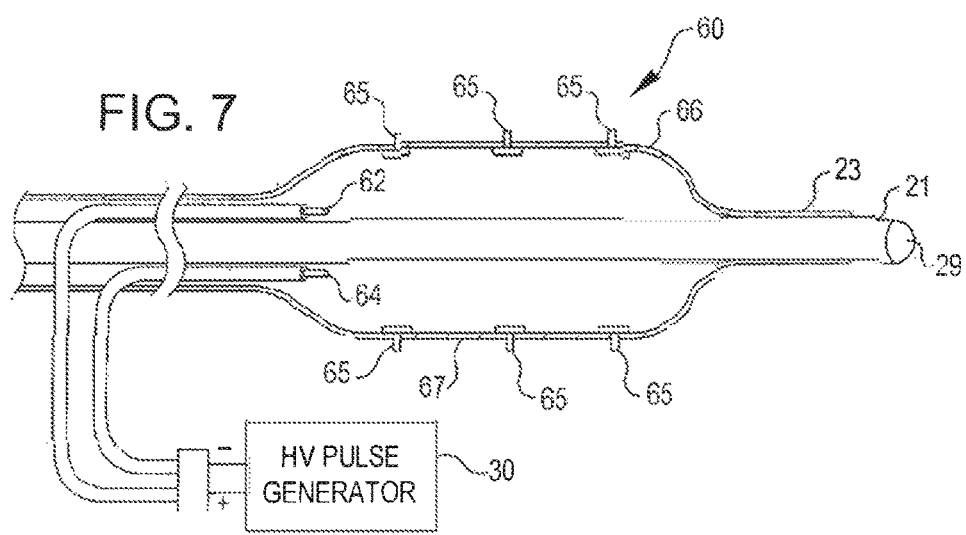
FIG. 7 is a side view of a dilating catheter with insulated electrodes within the balloon and studs to reach the calcification according to a still further embodiment of the invention.

FIG. 7 is another dilating 60 catheter with electrodes 62 and 64 within the balloon 66 and studs 65 to reach the calcification. The studs 65 form mechanical stress risers on the balloon surface 67 and are designed to mechanically conduct the shock wave through the intimal layer of tissue of the vessel and deliver it directly to the calcified lesion.

Figure 8:
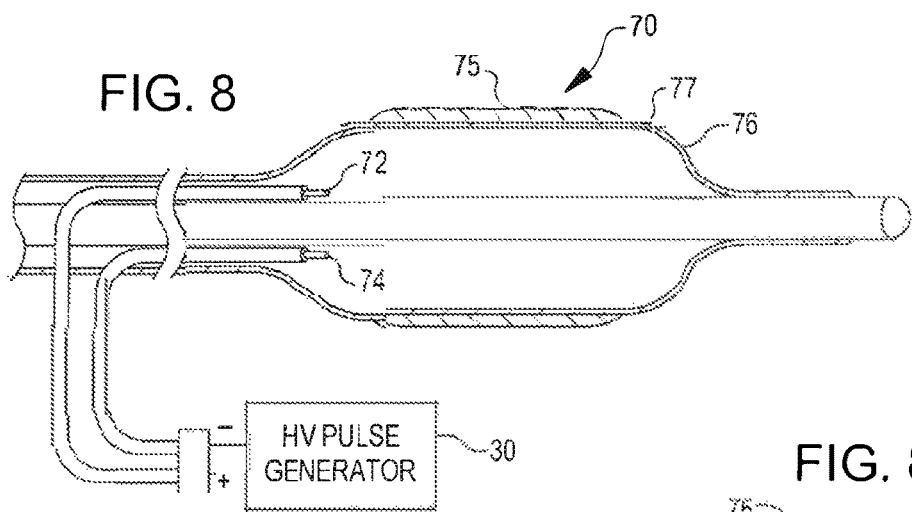
FIG. 8 is a side view of a dilating catheter with insulated electrodes within the balloon with raised ribs on the balloon according to still another embodiment of the invention.
Figure 8A:
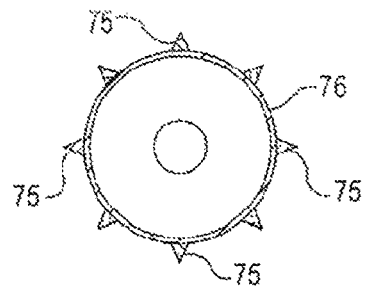
FIG. 8A is a front view of the catheter of FIG. 8.

FIG. 8 is another dilating catheter 70 with electrodes 72 and 74 within the balloon 76 and with raised ribs 75 on the surface 77 of the balloon 76. The raised ribs 75 (best seen in FIG. 8A) form stress risers that will focus the shock wave energy to linear regions of the calcified plaque.

Figure 9:
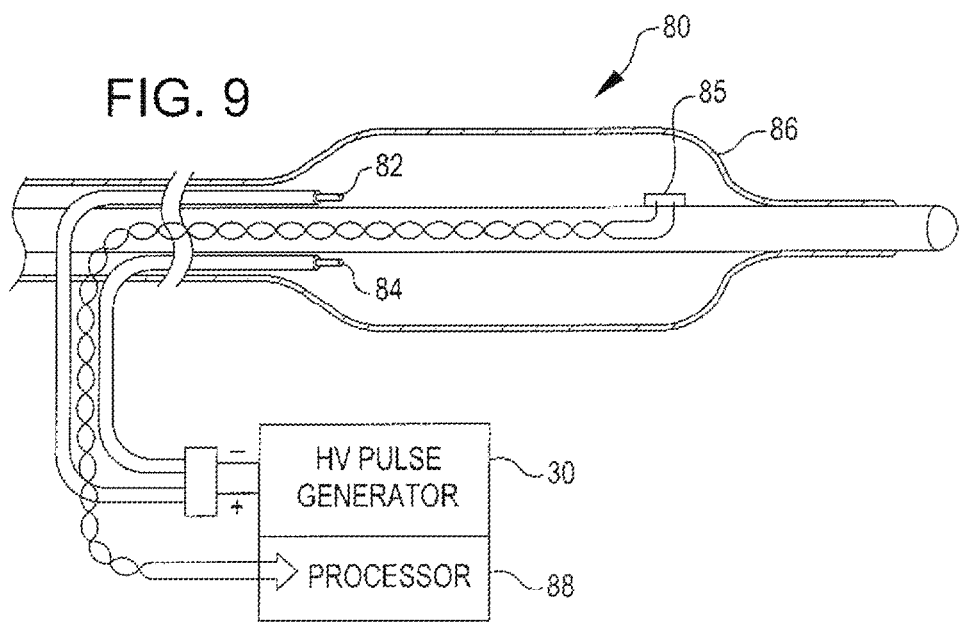
FIG. 9 is a side view of a dilating catheter with insulated electrodes within the balloon and a sensor to detect reflected signals according to a further embodiment of the invention.

FIG. 9 is a further dilating catheter 80 with electrodes 82 and 84 within the balloon 86. The catheter 80 further includes a sensor 85 to detect reflected signals. Reflected signals from the calcified plaque can be processed by a processor 88 to determine quality of the calcification and quality of pulverization of the lesion.

Figure 10:
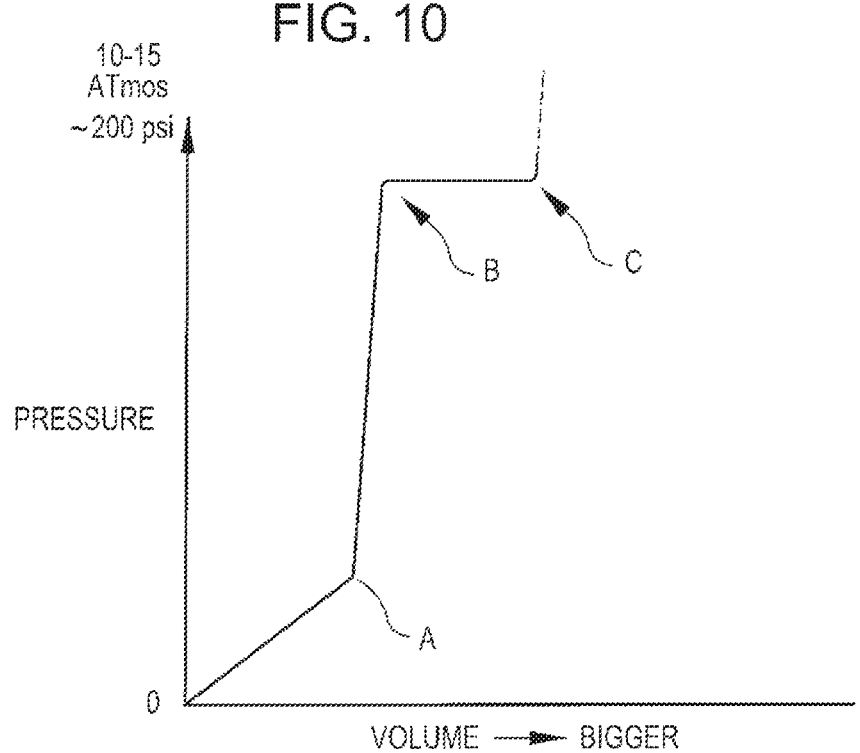
FIG. 10 is a pressure volume curve of a prior art balloon breaking a calcified lesion.
Figure 10A:
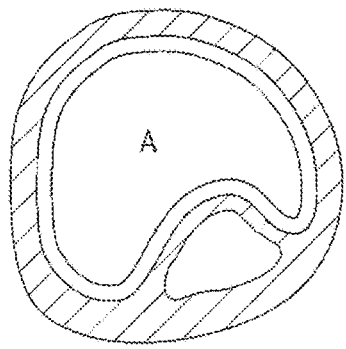
FIG. 10A is a sectional view of a balloon expanding freely within a vessel.
Figure 10B:
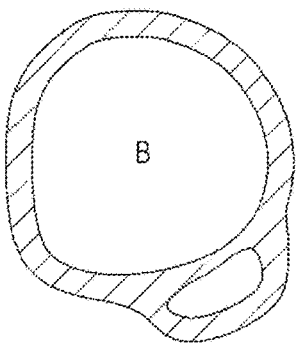
FIG. 10B is a sectional view of a balloon constrained to the point of breaking in a vessel.
Figure 10C:
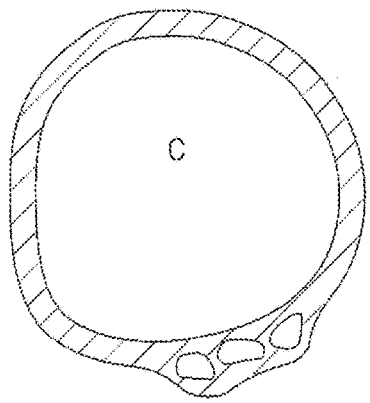
FIG. 10C is a sectional view of a balloon after breaking within the vessel.

FIG. 10 is a pressure volume curve of a prior art balloon breaking a calcified lesion. FIG. 10B shows the build up of energy within the balloon (region A to B) and FIG. 10C shows the release of the energy (region B to C) when the calcification breaks. At region C the artery is expanded to the maximum dimension of the balloon. Such a dimension can lead to injury to the vessel walls. FIG. 10A shows the initial inflation of the balloon.

Figure 11:
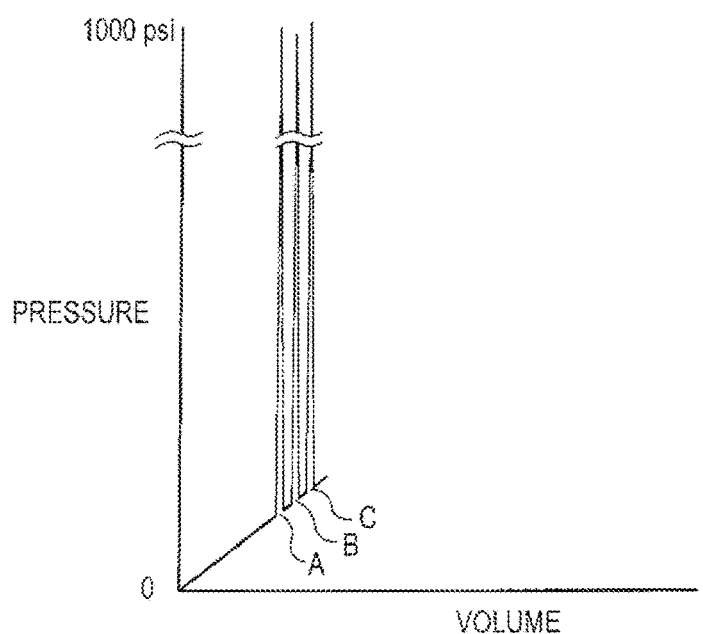
FIG. 11 is a pressure volume curve showing the various stages in the breaking of a calcified lesion with shock waves according to an embodiment of the invention.
Figure 11A:
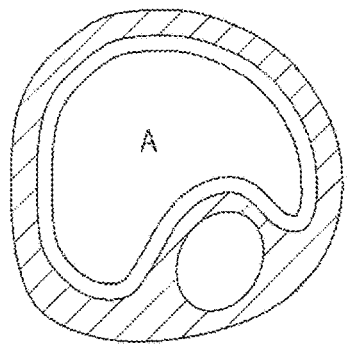
FIG. 11A is a sectional view showing a compliant balloon within a vessel.
Figure 11B:
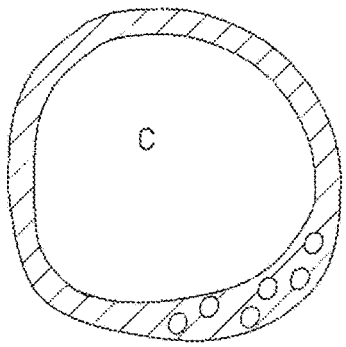
FIG. 11B is a sectional view showing pulverized calcification on a vessel wall.

FIG. 11 is a pressure volume curve showing the various stages in the breaking of a calcified lesion with shock waves according to the embodiment. The balloon is expanded with a saline fluid and can be expanded to fit snugly to the vessel wall (Region A)(FIG. 11A) but this is not a requirement. As the High Voltage pulses generate shock waves (Region B and C) extremely high pressures, extremely short in duration will chip away the calcified lesion slowly and controllably expanding the opening in the vessel to allow blood to flow un-obstructed (FIG. 11B).

Figure 12:
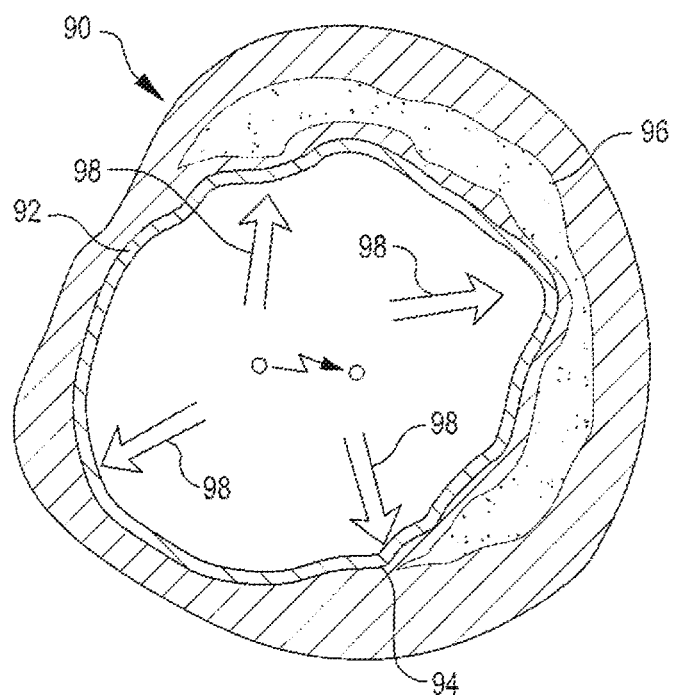
FIG. 12 illustrates shock waves delivered through the balloon wall and endothelium to a calcified lesion.

FIG. 12 shows, in a cutaway view, shock waves 98 delivered in all directions through the wall 92 of a saline filled balloon 90 and intima 94 to a calcified lesion 96. The shock waves 98 pulverize the lesion 96. The balloon wall 92 may be formed of non-compliant or compliant material to contact the intima 94.

Figure 13:
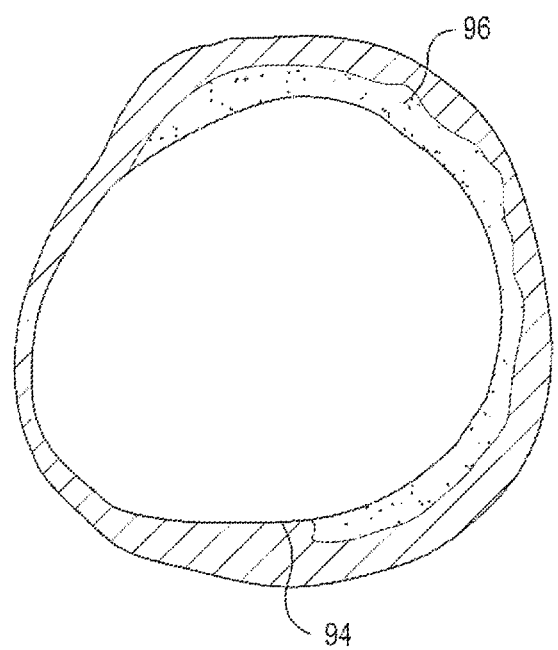
FIG. 13 shows calcified plaque pulverized and smooth a endothelium restored by the expanded balloon after pulverization.

FIG. 13 shows calcified plaque 96 pulverized by the shock waves. The intima 94 is smoothed and restored after the expanded balloon (not shown) has pulverized and reshaped the plaque into the vessel wall.

Figure 14:
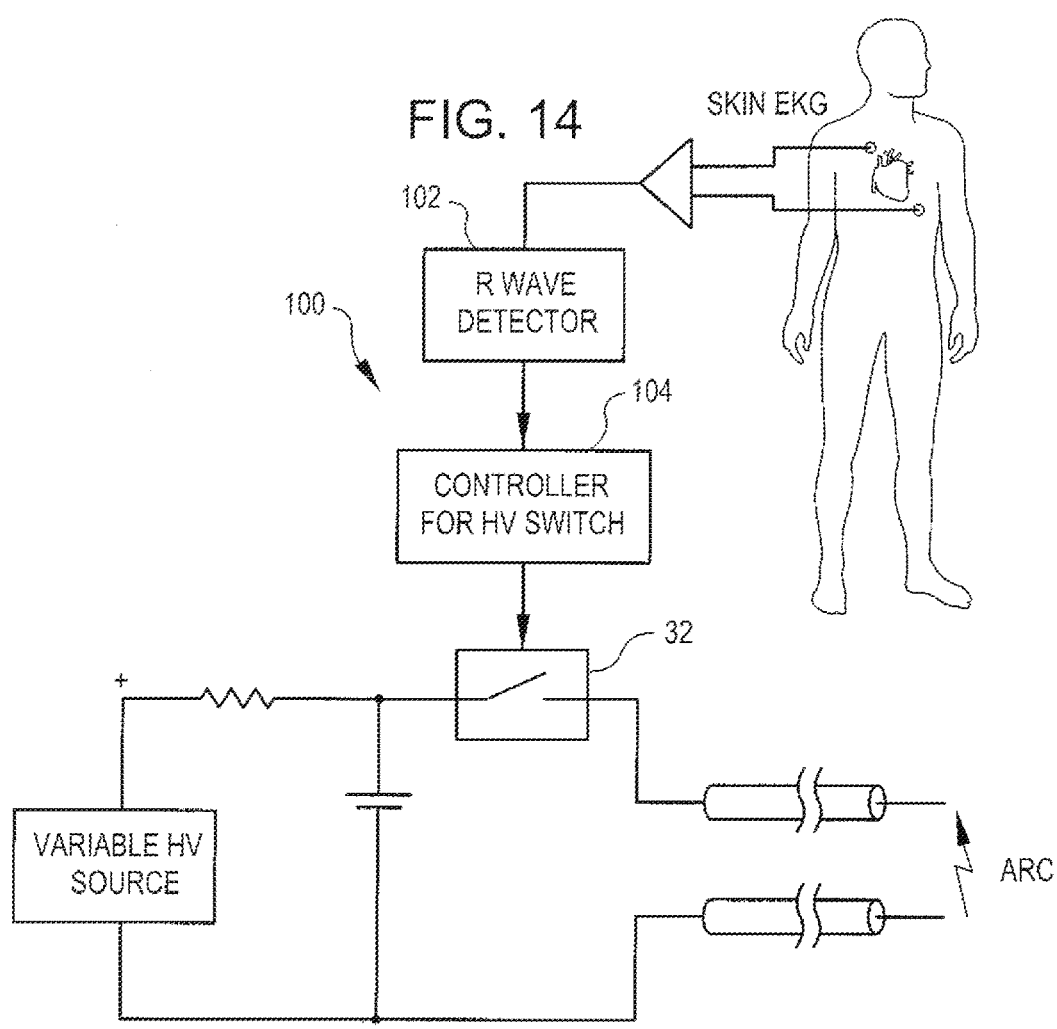
FIG. 14 is a schematic of a circuit that uses a surface EKG to synchronize the shock wave to the "R" wave for treating vessels near the heart.

FIG. 14 is a schematic of a circuit 100 that uses the generator circuit 30 of FIG. 3 and a surface EKG 102 to synchronize the shock wave to the "R" wave for treating vessels near the heart. The circuit 100 includes an R-wave detector 102 and a controller 104 to control the high voltage switch 32. Mechanical shocks can stimulate heart muscle and could lead to an arrhythmia. While it is unlikely that shock waves of such short duration as contemplated herein would stimulate the heart, by synchronizing the pulses (or bursts of pulses) with the R-wave, an additional degree of safety is provided when used on vessels of the heart or near the heart. While the balloon in the current drawings will provide an electrical isolation of the patient from the current, a device could be made in a non-balloon or non-isolated manner using blood as the fluid. In such a device, synchronization to the R-wave would significantly improve the safety against unwanted arrhythmias.

Figure 15:
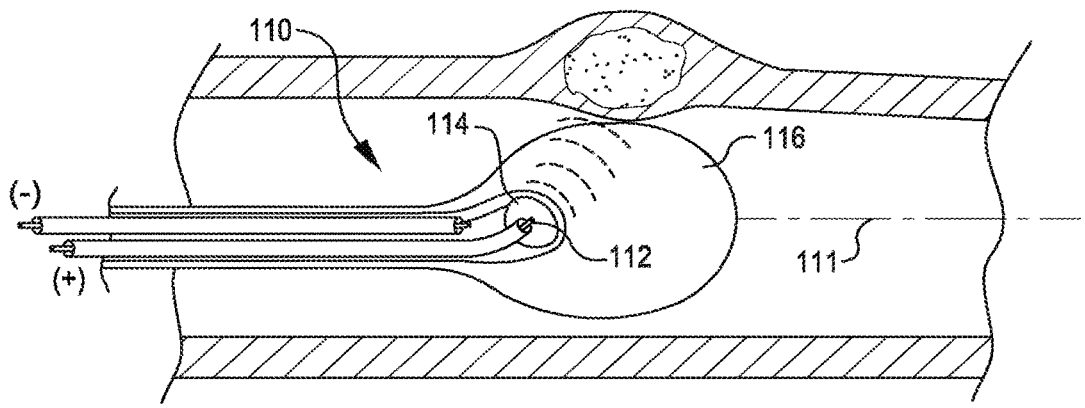
FIG. 15 is a side view, partly cut away, of a dilating catheter with a parabolic reflector acting as one electrode and provides a focused shock wave inside a fluid filled compliant balloon.

FIG. 15 shows a still further dilation catheter 110 wherein a shock wave is focused with a parabolic reflector 114 acting as one electrode inside a fluid filled compliant balloon 116. The other electrode 112 is located at the coaxial center of the reflector 114. By using the reflector as one electrode, the shock wave can be focused and therefore pointed at an angle (45 degrees, for example) off the center line 111 of the catheter artery. In this configuration, the other electrode 112 will be designed to be at the coaxial center of the reflector and designed to arc to the reflector 114 through the fluid. The catheter can be rotated if needed to break hard plaque as it rotates and delivers shock waves.

Figure 16:
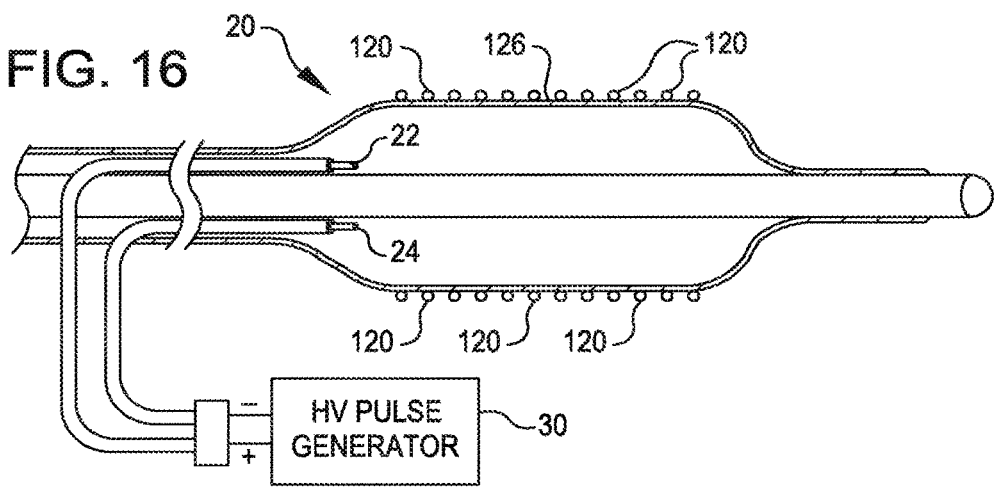
FIG. 16 is a shock wave angioplasty balloon similar to FIG. 2 with micro-balloons or microspheres filled with a drug on the surface of the balloon.

FIG. 16 shows a shock wave balloon 126 similar to FIG. 2 with microspheres or microcapsules 120 attached to the surface. Such micro spheres may contain an antiproliferative drug such as Paclitaxel, Serolimus or Evrolimus or other similar drug. The spheres may be designed to be rigid and resist breaking when exposed to normal balloon inflation pressures of several atmospheres. However, when exposed to high pressure shock waves, the microspheres will break and release the drug contained within. Shock waves delivered from such a balloon have the added advantage of creating a permeable cell wall membrane which aides in the transfer of the released drug to the walls of the vessel. Such drugs are known to reduce the restenosis rate in vessels treated. These micro-encapsulations can range in size typically from 2 to 100 microns in diameter although the size is not critical if they are small relative to the balloon size. The material can be a rigid polymer, a starch, glucose or any number of materials chosen to crack when exposed to shock waves and resist cracking when exposed to normal pressures of an angioplasty dilation procedure.

Figure 17:
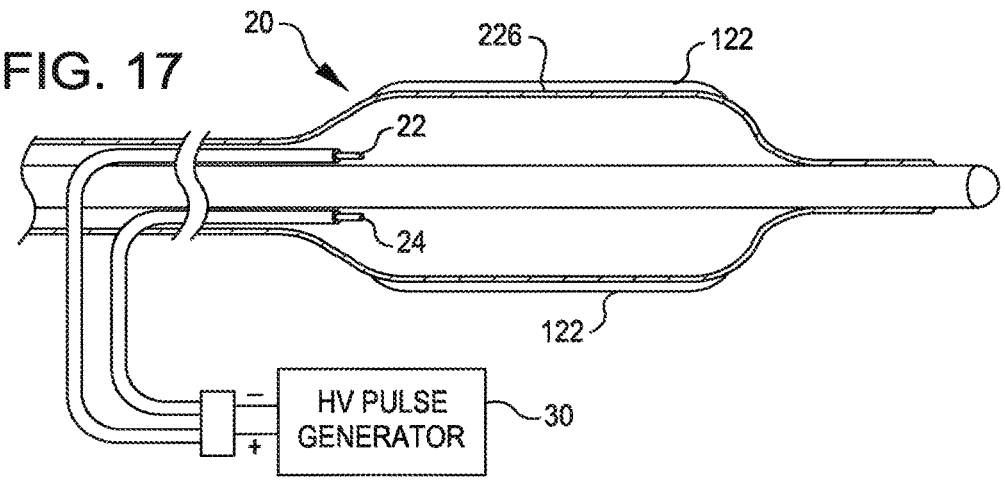
FIG. 17 is a layered shock wave balloon similar to FIG. 2 with an added layer of drug bonded to the balloon.

FIG. 17 is a layered shock wave balloon 226 similar to FIG. 2 with an added layer 122 of drug chemically bonded to the balloon. The drug is released from its bond to the balloon material by the mechanical force of a shock wave. Thus the drug (paclitaxel for example) will be released at the site of a lesion while the lesion is being expanded with the predilitation balloon. As with the micro-encapsulated drug the shock waves from the balloon can also create a permeable cell wall membrane aiding in the drug uptake in the vessel wall.

In the embodiment discussed above, the drug is chemically bonded to the outer surface of the balloon and the shock wave facilitates its release from the balloon wall. In another embodiment of the subject invention, the drug is applied to the balloon in a manner such that it will be released into the lesion site when the balloon is inflated. The latter arrangement was typical for drug coated balloons of the prior art that did not include a shock wave generator.

Accordingly, in this approach, a self-releasing drug is coated on the balloon wall. The collapsed balloon is advanced to the treatment site and then be gently inflated. The amount of pressure applied to the balloon is preferably fairly low, on the order of 1 to 4 atmospheres. The goal would be to inflate the balloon to create intimate contact between the balloon and the wall of the vessel to cause most or at least a large portion of the drug to be released towards the tissue to be treated. Preferably, the high pressures used to attempt to crack the calcified lesions are not applied.

Once the balloon has been inflated and the drug at least partially released, the shock wave generator can be activated. The shock waves create cracks in the calcified lesion opening a pathway for the drug to reach the targeted tissue, typically situated behind the calcification in the wall of the vessel. In addition, the shock waves may help to drive the drug into the tissue. Still further, the shock waves can increase the permeability of the cell wall membrane aiding in the update of the drug. Thus, it can be appreciated that providing a shock wave generator inside a drug covered balloon can be useful even if the shock waves are not the primary mechanism used to release the drug from the balloon.

In this approach, the drug could also be in the form of microspheres or microcapsules. The microspheres or microcapsules could be applied to the balloon wall and released upon partial inflation of the balloon. In this case, the shock waves could further function to break microspheres or microcapsules, releasing the drug into the vessel.

Once the calcification in the lesion has been cracked, the balloon can be further inflated. This additional inflation could contribute to a further release of the drug into the vessel wall.

It should also be noted that the drugs would commonly (but not necessarily) be applied to the balloon wall with an excipient for the purpose of long-term stabilization, bulking up solid formulations that contain potent active ingredients (thus often referred to as "bulking agents", "fillers", or "diluents"), or to confer a therapeutic enhancement on the active ingredient in the final dosage form, such as facilitating drug absorption, reducing viscosity, or enhancing solubility. Excipients can also be useful in the manufacturing process, to aid in the handling of the active substance concerned such as by facilitating powder flowability or non-stick properties, in addition to aiding in vitro stability such as prevention of denaturation or aggregation over the expected shelf life. The selection of appropriate excipients also depends upon the route of administration and the dosage form, as well as the active ingredient and other factors.

While particular embodiments of the present invention have been shown and described, modifications may be made. It is therefore intended in the appended claims to cover all such changes and modifications which fall within the true spirit and scope of the invention as defined by those claims.

What is claimed is:

1. A method for treating calcified lesions in a blood vessel comprising:
    providing a catheter having an elongated carrier, a balloon carried by the elongated carrier in sealed relation thereto, a shock wave generator within the balloon, and a medicinal agent applied to the outer surface of the balloon in a manner such that the medicinal agent is at least partially released when the balloon is inflated into contact with the wall of a blood vessel;
    inserting the catheter into a blood vessel to be treated;
    inflating the balloon with a liquid to a pressure sufficient to create contact between the outer surface of the balloon and the wall of the blood vessel causing the release of a portion of the medicinal agent from the balloon without the generation of shock waves;
    generating a shock wave within the balloon to crack calcified lesions in the blood vessel with the balloon remaining sealed both during and after the creation of the shock wave; and
    after the generating step, further inflating the balloon with the liquid to further release the medicinal agent.

2. The method of claim 1, wherein during the initial inflating step, the balloon is pressurized to between 1 and 4 atmospheres.

3. The method of claim 1 wherein the shock wave is generated by supplying a high voltage pulse to a pair of electrodes located within the balloon to produce a plasma arc which in turn creates a mechanical shock wave within the balloon.

4. The method of claim 1 wherein the medicinal agent is in the form of a drug coated on the outer surface of the balloon wall.

5. The method of claim 1 wherein the medicinal agent is coated on the outer surface of the balloon with an excipient.

6. The method of claim 1, wherein the medicinal agent is contained within a plurality of microspheres.

7. The method of claim 1, wherein the medicinal agent is a drug contained within a plurality of microcapsules, wherein the drug is releasable from the plurality of microcapsules in response to the shock wave.

* * * * *